United States Patent
Lunts et al.

(10) Patent No.: US 6,984,514 B2
(45) Date of Patent: Jan. 10, 2006

(54) BACTERIUM HAVING ABILITY TO PRODUCE L-GLUTAMIC ACID, L-PROLINE OR L-ARGININE AND METHOD FOR PRODUCING L-GLUTAMIC ACID, L-PROLINE OR L-ARGININE

(75) Inventors: Maria Grigorievna Lunts, Moscow (RU); Svetlana Aleksandrovna Fomina, Moscow (RU); Tatyana Viktorovna Leonova, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 130 days.

(21) Appl. No.: 09/953,298

(22) Filed: Sep. 17, 2001

(65) Prior Publication Data

US 2002/0058315 A1  May 16, 2002

(30) Foreign Application Priority Data

Sep. 26, 2000 (RU) ............................. 2000124295

(51) Int. Cl.
*C12N 1/20* (2006.01)
*C12P 13/04* (2006.01)

(52) U.S. Cl. ................. 435/252.8; 435/252.33; 435/488; 435/114; 435/107; 435/106; 435/110; 435/481

(58) Field of Classification Search ............. 435/481, 435/110, 106, 107, 114, 488, 252.33, 252.8
See application file for complete search history.

(56) References Cited

U.S. PATENT DOCUMENTS 3,902,967 A * 9/1975 Chibata et al. ............. 435/114
4,278,765 A * 7/1981 Debabov et al. ............ 435/481
5,393,671 A    2/1995 Tujimoto et al.
5,908,768 A    6/1999 Ono et al.

FOREIGN PATENT DOCUMENTS

GB     2 080 825    2/1982

OTHER PUBLICATIONS

Iaccarino et al., J. Bacteriology (1971), 105(2), 527-37.*
Berg et al., GENETICS, (Oct. 1979) 93 (2) 308-19.*
K. Sano, et al., Chemical Abstracts, 1 page, AN 1968:75876, "Microbial Production of L-Lysine. I. Production by Auxotrophs of Brevibacterium Flavum", 1968.
R. Kraemer, Journal of Biotechnology, vol. 45, No. 1, pp. 1-21, "Genetic and Physiological Approaches for the Production of Amino Acids", 1996.
U.S. Appl. No. 10/924,798, filed Aug. 25, 2004, Gusyatiner et al.

* cited by examiner

Primary Examiner—Irene Marx
(74) Attorney, Agent, or Firm—Oblon, Spivak, McClelland, Maier & Neustadt, P.C.

(57) ABSTRACT

L-Glutamic acid, L-proline or L-arginine is produced by culturing a bacterium belonging to the genus Escherichia, which is L-isoleucine auxotrophic and has ability to produce L-glutamic acid, L-proline or L-arginine, in a medium containing L-isoleucine, to produce and accumulate L-glutamic acid, L-proline or L-arginine in a culture, and collecting L-glutamic acid, L-proline or L-arginine from the culture.

6 Claims, No Drawings

BACTERIUM HAVING ABILITY TO PRODUCE L-GLUTAMIC ACID, L-PROLINE OR L-ARGININE AND METHOD FOR PRODUCING L-GLUTAMIC ACID, L-PROLINE OR L-ARGININE

BACKGROUND OF THE INVENTION

The present invention relates to techniques in the field of microbial industry. In particular, the present invention relates to a method for producing L-glutamic acid, L-proline or L-arginine by fermentation, and a bacterium used in the method. L-Glutamic acid, L-arginine and L-proline are important as food, medicine and the like.

L-Arginine and L-proline are synthesized by *E. coli* cells from a common precursor, L-glutamic acid. Therefore, the level of the production of L-arginine or L-proline depends on availability of their common precursor, L-glutamic acid.

There are known strains of *E. coli* having an increased level of L-glutamic acid synthesis. In particular, mutants which are derived from *E. coli* K12 strain and are deficient or decrease in 2-ketoglutarate dehydrogenase activity, can produce L-glutamic acid with a fairly high productivity (U.S. Pat. Nos. 5,393,671 and 5,908,768).

It is known as well that some *E. coli* mutants can produce L-arginine and L-proline. They were obtained as mutants resistant to analogs of those amino acids and by cloning of some genes important for their biosynthesis (UK patent publication No. 2080825A).

SUMMARY OF THE INVENTION

An object of the present invention is to provide a novel bacterium having ability to produce L-glutamic acid, L-proline or L-arginine and a method for producing L-glutamic acid, L-proline or L-arginine by using the bacterium having ability to produce L-glutamic acid, L-proline or L-arginine.

The present inventors found that L-isoleucine auxotrophs of *E. coli* having a deficiency in an ilvA gene, produced L-glutamic acid. Besides, strains having a deficiency in an ilvA gene, can be used as parent strains for breeding of producers of L-proline and L-arginine. In other words, the present inventors found that L-isoleucine auxotrophy can be used for improvement of producers of L-glutamic acid, L-proline or L-arginine. Thus, the present invention has been accomplished.

The present invention provides the followings.

(1) An *Escherichia* bacterium which is L-isoleucine auxotrophic and has ability to produce L-glutamic acid, L-proline or L-arginine.

(2) The *Escherichia* bacterium according to (1), which is deficient in any one of activities of L-isoleucine biosynthesis enzymes.

(3) The *Escherichia* bacterium according to (2), which is deficient in threonine deaminase activity.

(4) The *Escherichia* bacterium according to any one of (1) to (3), which is *Escherichia coli*.

(5) A method for producing L-glutamic acid, L-proline or L-arginine, which comprises culturing the Escherichia bacterium as defined in any one of (1) to (4) in a medium containing L-isoleucine, to produce and accumulate L-glutamic acid, L-proline or L-arginine in a culture and collecting L-glutamic acid, L-proline or L-arginine from the culture.

DETAILED DESCRIPTION OF THE INVENTION

<1> Bacterium of the Present Invention

The bacterium of the present invention is a bacterium belonging to the genus *Escherichia*, which is L-isoleucine auxotrophic and has ability to produce L-glutamic acid, L-proline or L-arginine. An example of the *Escherichia* bacterium is *Escherichia coli*.

The expression "a bacterium has ability to produce L-glutamic acid, L-proline or L-arginine" means that the bacterium accumulates a significant amount of L-glutamic acid, L-proline or L-arginine in a medium when the bacterium is cultured in the medium, or increases the content of L-glutamic acid, L-proline or L-arginine in the bacterium. The expression "a bacterium is L-isoleucine auxotrophic" means that the bacterium requires L-isoleucine (usually, not less than 10 mg/l) in a medium for growth.

The bacterium of the present invention produces at least L-glutamic acid, L-proline or L-arginine and may produce two or more types of L-amino acids.

The bacterium of the present invention can be obtained by imparting L-isoleucine auxotrophy to an *Escherichia* bacterium having ability to produce L-glutamic acid, L-proline or L-arginine, or by imparting ability to produce L-glutamic acid, L-proline or L-arginine to an L-isoleucine auxotrophic *Escherichia* bacterium.

In order to impart the L-isoleucine auxotrophy, there can be used a method comprising subjecting *Escherichia* bacteria to mutagenesis, allowing the *Escherichia* bacteria to form colonies on an agar medium containing L-isoleucine, replicating the colonies to an agar medium not containing L-isoleucine, and selecting strains that cannot grow on the agar medium not containing L-isoleucine. The mutagenesis includes UV irradiation and treatments with mutagenesis agents used for usual mutagenesis treatments such as N-methyl-N'-nitro-N-nitrosoguanidine (NTG) and nitrous acid. Alternatively, naturally occurring mutants may be selected.

The isoleucine auxotrophy is preferably due to a deficiency in any of L-isoleucine biosynthetic enzyme activities (activities of enzymes catalyzing reactions of L-isoleucine biosynthesis). The L-isoleucine biosynthetic enzymes includes threonine deaminase, acetohydroxyacid synthase, acetohydroxy-acid isomeroreductase, dihydroxy-acid dehydratase. It is preferred that threonine deaminase activity is deficient. The expression "activity is deficient" usually means that the intracellular activity of the enzyme is lower than that of a wild type strain, and when a strain in which the activity of the enzyme is deficient is obtained by modification using gene recombinant techniques or the like, the intracellular activity of the enzyme is lower than that of the strain before the modification.

In order to obtain the deficiency of the enzyme activity as mentioned above, a mutation causing the deficiency of the enzyme activity can be introduced into a gene encoding the enzyme by a conventional mutagenesis technique or genetic engineering technique.

Examples of the mutagenesis technique include, for example, the method utilizing irradiation of X-ray or ultraviolet light, the method utilizing treatment with a mutagenic agent such as N-methyl-N'-nitro-N-nitrosoguanidine and the like. The site of gene to which a mutation is introduced may be a coding region encoding an enzyme protein, or an expression regulatory region such as a promoter.

Examples of the genetic engineering technique include, for example, genetic recombination, genetic transduction, cell fusion and the like. For example, a drug resistance gene is inserted into a target gene to produce a functionally inactivated gene (defective gene). Then, this defective gene is introduced into a cell of a microorganism belonging to the genus *Escherichia*, and the target gene on a chromosome is replaced with the defective gene by homologous recombination (gene disruption).

Whether a microorganism decreases in an activity of a target enzyme or is deficient in the activity, and degree of the decrease of the activity can be determined by measuring the enzyme activity of a bacterial cell extract or a purified fraction of a candidate strain, and comparing it with that of a wild type strain or a parent strain. Depending on the target enzyme, a target variant can be selected based on a phenotype of the variant.

In order to impart ability to produce L-glutamic acid, L-proline or L-arginine, there can be used methods conventionally adopted for breeding *Escherichia* bacteria or the like, such as those methods for obtaining auxotrophic mutant strains, strains resistant to L-amino acid analogues or metabolic control mutant strains, and methods for producing recombinant strains wherein L-amino acid biosynthetic enzyme activities are enhanced (see "Amino Acid Fermentation", the Japan Scientific Societies Press [Gakkai Shuppan Center], 1st Edition, published on May 30, 1986, pp.77 to 100). In breeding of amino acid-producing bacteria, the characteristic such as auxotrophy, L-amino acid analogue resistance and metabolic control mutation may be imparted alone or in combination of two or more. The L-amino acid biosynthetic enzyme activity may be enhanced alone or in combination of two or more. Further, imparting of the characteristic such as auxotrophy, L-amino acid analogue resistance and metabolic control mutation may be combined with enhancement of the L-amino acid biosynthesis enzyme activity.

For example, L-glutamic acid-producing bacteria can be bred as mutants exhibiting auxotrophy for oleic acid or the like.

Also, L-glutamic acid-producing ability can be imparted by, for example, introducing a DNA that codes for any one of enzymes including glutamate dehydrogenase (Japanese Patent Application Laid-open (Kokai) 61-268185/1986), glutamine synthetase, glutamate synthase, isocitrate dehydrogenase (Japanese Patent Application Laid-open (Kokai) Nos. 62-166890/1987 and 63-214189/1988), aconitate hydratase (Japanese Patent Application Laid-open (Kokai) No. 62-294086/1987), citrate synthase (Japanese Patent Application Laid-open (Kokai) Nos. 62-201585/1987 and 63-119688/1988), phosphoenolpyruvate carboxylase (Japanese Patent Application Laid-open (Kokai) Nos. 60-87788/1985 and 62-55089/1987), pyruvate dehydrogenase, pyruvate kinase, phosphoenolpyruvate synthase, enolase, phosphoglyceromutase, phosphoglycerate kinase, glyceraldehyde-3-phosphate dehydrogenase, triose phosphate isomerase, fructose bisphosphate aldolase, phosphofructokinase (Japanese Patent Application Laid-open (Kokai) No. 63-102692/1988), glucose phosphate isomerase, glutamine-oxoglutarate aminotransferase (WO99/07853) and so forth.

Further, the bacterium of the present invention may be made to be deficient in activity of an enzyme that catalyzes a reaction for generating a compound other than L-glutamic acid by branching off from the biosynthetic pathway of L-glutamic acid. The enzyme that catalyzes the reaction for generating the compound other than L-glutamic acid by branching off from the biosynthetic pathway L-glutamic acid include α-ketoglutarate dehydrogenase, isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase and so forth.

L-Proline-producing ability can be imparted by, for example, making the bacterium have γ-glutamyl kinase desensitized in feedback inhibition by L-proline, and/or by destroying the L-proline degradation system. The method for making the bacterium have γ-glutamyl kinase desensitized in feedback inhibition by L-proline is exemplified by a method comprising introducing a DNA coding for γ-glutamyl kinase desensitized in feedback inhibition by L-proline into cells (J. Bacteriol. 170, 5943 (1988)). The method for destroying the L-proline degradation system is exemplified by a method comprising introducing a mutation in a proline dehydrogenase gene so that no active proline dehydrogenase is expressed. Also, the bacterium in which the L-proline degradation system is destroyed can be obtained by obtaining a strain deficient in L-proline-assimilating ability and selecting a strain extracellularly produce L-proline from the obtained strains by using L-proline auxotrophy as an index.

L-Arginine-producing ability can be imparted by, for example, imparting resistance to α-methylmethionine, p-fluorophenylalanine, D-arginine, arginine hydroxamate, S-(2-aminoethyl)-cysteine, α-methylserine, β-2-thienylalanine or sulfaguanidine (Japanese Patent Application Laid-Open No. 56-106598), or introducing an argA gene coding for N-acetylglutamate synthase (Japanese Patent Application Laid-Open No. 57-5693).

<2> Method of the Present Invention

The method of the present invention comprises culturing the bacterium of the present invention in a medium containing L-isoleucine, to produce and accumulate L-glutamic acid, L-proline or L-arginine in a culture and collecting L-glutamic acid, L-proline or L-arginine from the culture.

The medium may be an ordinary medium containing a carbon source, a nitrogen source, inorganic ions and optionally other organic components, provided that it contains L-isoleucine. The amount of L-isoleucine is one sufficient to allow the bacterium of the present invention to produce and accumulate L-glutamic acid, L-proline or L-arginine, and is usually 25 to 250 mg/l.

As the carbon source, it is possible to use sugars such as glucose, lactose, galactose, fructose, and starch hydrolysate; alcohols such as glycerol and sorbitol; or organic acids such as fumaric acid, citric acid and succinic acid.

As the nitrogen source, it is possible to use inorganic ammonium salts such as ammonium sulfate, ammonium chloride and ammonium phosphate; organic nitrogen such as soybean hydrolysate; ammonia gas; or aqueous ammonia.

It is preferable to allow required substances such as vitamin $B_1$ or yeast extract to be contained in appropriate amounts as organic trace nutrients. Other than the above, potassium phosphate, magnesium sulfate, iron ion, manganese ion and the like are added in small amounts, if necessary.

Cultivation is preferably carried out under an aerobic condition for 16 to 72 hours. The cultivation temperature is controlled at 25° C. to 45° C., and pH is controlled at 5 to 8 during cultivation. Inorganic or organic, acidic or alkaline substances as well as ammonia gas or the like can be used for pH adjustment.

The culture includes a medium and cells, and is preferably a medium.

Collection of L-glutamic acid, L-proline or L-arginine from the culture may be usually carried out by combining an ion exchange resin method, a precipitation method and other known methods.

EXAMPLES

The present invention will further specifically be explained with reference to the following examples hereafter.

Example 1

Production of L-glutamic Acid by ilvA Deficient Strain

A) Utilization of an insertion of transposon Tn5 (or any other) into the ilvA gene Cells of the *E. coli* strain K12 of wild type (VKPM B-7) were treated with a bacteriophage P1 which was grown on cells of L-isoleucine auxotrophic strain *E. coli* C600 ilvA::Tn5 having the insertion of transposon Tn5 into the ilvA gene, and placed on LB agar plates, containing kanamycin (20 µg/ml), for selection of kanamycin resistant transductants. As a result, a derivative of the wild type strain of *E. coli* K12 having insertion of transposon Tn5 into the ilvA gene was obtained. This strain was named B7ILE, and has been deposited in the Russian National Collection of Industrial Microorganisms (VKPM) since Jul. 18, 2000 and converted to a deposit under the Budapest Treaty on May 18, 2001, and the accession number VKPM B-8013 is given.

B) Construction of an ilvA deficient derivative from the wild type strain *E. coli* K12, having a mutation in the ilvA gene The strain VL334 (VKPM B-1641) is an L-isoleucine and L-threonine auxotrophic strain having mutations in thrC and ilvA genes (U.S. Pat. No. 4,278,765). A wild type allele of thrC gene was transferred by the method of general transduction using a bacteriophage P1 grown on cells of the wild type *E. coli* strain K12 (VKPM B-7). As a result, an L-isoleucine auxotrophic strain VL334thrC+ was obtained. The strain VL334thrC+ was deposited in the Russian National Collection of Industrial Microorganisms (VKPM) on Dec. 6, 2004, converted to a deposit under the Budapest Treaty on Dec. 8, 2004, and assigned the accession number VKPM B-8961.

C) Production of L-glutamic acid by the L-isoleucine auxotrophic strain in test-tube fermentation The fermentation medium contained 60 g/l glucose, 25 g/l ammonium sulfate, 2 g/l $KH_2PO_4$, 1 g/l $MgSO_4$, 0.1 mg/l thiamine, 50 mg/l L-isoleucine and 25 g/l chalk (pH 7.2). Glucose and chalk were sterilized separately. 2 ml of the medium was placed into test tubes, and inoculated with one loop of the tested microorganisms, and the cultivation was carried out at 37° C. for 2 days with shaking. The results are shown in Table 1.

TABLE 1

| Strain | Phenotype | Accumulation of L-glutamic acid (g/l) |
|---|---|---|
| K12 (VKPM B-7) | Wild type | <0.1 |
| B7ILE (VKPM B-8013) | IlvA::Tn5 | 2.0 |
| VL334thrC+ | IlvA442 | 12.0 |

Example 2

Production of L-proline by an ilvA Deficient L-proline Producer

The cells of wild type strain *E. coli* K12 (VKPM B-7) was treated with a mutagen, N-methyl-N'-nitro-N-nitrosoguanidine (0.1 mg/ml), for 20 min at 37° C., washed and plated on minimal agar medium M9 supplemented with 1.25 mg/ml tryptone, 10 mg/ml L-proline and 0.05 mg/ml 2,3,5-triphenyltetrazolium chloride. Most colonies arisen after 3 day of incubation at 37° C. were colored red. A few colonies, which could not oxidize L-proline, were white. One of such colonies was used as a parent for obtaining mutants resistant to proline analogs (3,4-dehydroxyproline and azetidine-2-carboxylate) which were added into M9 agar medium in concentration of 2 mg/ml each.

Some of mutants arisen could produce L-proline. The best L-proline producer 702 was treated with a P1 bacteriophage grown on cells of the strain TG1 in which the gene ilvA was disrupted by the insertion of chloramphenicol (Cm) resistance ($Cm^r$) gene. One of obtained Cm resisitant transductant, 702ilvA, which turned to be L-isoleucine auxotroph, was much more effective L-proline prouducer than the L-isoleucine prototrophic parent strain 702 (Table 2). The fermentation was carried out as indicated in Example 1.

TABLE 2

| Strain | Phenotype | Accumulation of L-proline (g/l) |
|---|---|---|
| K12 (VKPM B-7) | Wild type | <0.1 |
| 702 (VKPM B-8011) | Defective L-proline degradation, resistance to proline analogs | 0.5 |
| 702ilvA (VKPM B-8012) | Defective L-proline degradation, resistance to proline analogs, L-isoleucine auxotroph, $Cm^r$ | 8 |

The strains 702 and 702ilvA have been deposited in the Russian National Collection of Industrial Microorganisms (VKPM) since Jul. 18, 2000 and converted to a deposit under the Budapest Treaty on May 18, 2001 and the accession numbers VKPM B-8011 And VKPM B-8012 are given, respectively.

Example 3

Production of L-arginine by an ilvA Deficient L-arginine Producer

The strain 237, an L-arginine-producing strain, which have been selected as mutant resistant to a pyrimidine analog, 6-azauracil, has insertion of the transposon Tn5 into the ilvA gene and, therefore, it is an L-isoleucine auxotroph. The strain 237 has been deposited in the Russian National Collection of Industrial Microorganisms (VKPM) since Apr. 10, 2000 and converted to a deposit under the Budapest Treaty on May 18, 2001, and the accession number VKPM B-7925 is given.

Cells of the strain 237 were treated with a P1 bacteriophage grown on cells of the wild type *E. coli* K12 strain (VKPM B-7), and L-isoleucine prototrophic transformants were selected. The L-arginine production of all L-isoleucine prototrophic transductants was drastically decreased (Table 3). The fermentation was carried out as indicated in Example 1.

TABLE 3

| Strain | Phenotype | Accumulation of L-arginine (g/L) |
|---|---|---|
| K12 (VKPM B-7) | Wild type | <0.1 |
| 237 (VKPM B-7925) | Resistant to 6-azauracil, L-isoleucine auxotroph, ilvA::Tn5, $Km^r$ | 4.5 |
| 237ilvA$^+$ | Resistant to 6-azauracil, ilvA$^+$ | 0.4–0.6 |

What is claimed is:

1. A biologically pure culture of an *Escherichia coli* bacterium, which is a strain selected from the group consisting of strain 702, accession number VKPM B-8011, and strain 702ilvA, accession number VKPM B-8012.

2. A biologically pure culture of an *Escherichia coli* bacterium, which is strain 237, accession number VKPM B-7925.

3. A biologically pure culture of an *Escherichia coli* bacterium, which is a strain, selected from the group consisting of strain B7ILE, accession number VKPM B-8013, and strain VL334thrC$^+$, accession number VKPM B-8961.

4. A method for producing L-proline, which comprises culturing the *Escherichia coli* bacterium of claim 1 in a culture medium containing L-isoleucine, to produce and accumulate L-proline in the culture medium, and collecting L-proline from the culture medium.

5. A method for producing L-arginine, which comprises culturing the *Escherichia coli* bacterium of claim 2 in a culture medium containing L-isoleucine, to produce and accumulate L-arginine in the culture medium, and collecting L-arginine from the culture medium.

6. A method for producing L-glutamic acid, which comprises culturing the *Escherichia coli* bacterium of claim 3 in a culture medium containing L-isoleucine, to produce and accumulate L-glutamic acid in the culture medium, and collecting L-glutamic acid from the culture medium.

* * * * *